United States Patent

Grigoletto

[11] Patent Number: 5,620,455
[45] Date of Patent: Apr. 15, 1997

[54] MULTI-FUNCTION INSTRUMENT FOR PEDICURE OPERATIONS OR THE LIKE

[76] Inventor: Luigina Grigoletto, Via Monte Nero 18/A, 36027 Cusinati di Rosa' (Prov. of Vicenza), Italy

[21] Appl. No.: 451,623

[22] Filed: May 26, 1995

[30] Foreign Application Priority Data

Jun. 2, 1994 [IT] Italy ................. PD94A0102

[51] Int. Cl.$^6$ ................................. A61B 17/32
[52] U.S. Cl. .................. 606/167; 606/131; 132/73
[58] Field of Search ................ 606/167, 131, 606/168, 169, 132; 132/73, 75.6, 75.8, 73.5

[56] References Cited

U.S. PATENT DOCUMENTS 2,425,665 8/1947 Arden ........................ 606/167
4,643,207 2/1987 Grahame ..................... 132/73

FOREIGN PATENT DOCUMENTS

| 0202139 | 4/1986 | European Pat. Off. ....... A45D 29/00 |
| 907702 | 1/1981 | France . |
| 8763525 | 7/1987 | Germany . |
| 2050840 | 1/1981 | United Kingdom . |
| 658916 | 11/1986 | United Kingdom . |

*Primary Examiner*—Michael Buiz
*Assistant Examiner*—Kevin Truong
*Attorney, Agent, or Firm*—Guido Modiano; Albert Josif

[57] ABSTRACT

Multi-function instrument for pedicure operations and manicure operations, which comprises a body having at least one grip region and at least one coupling region for at least one main blade-like tool, characterized in that it comprises at least one cap for covering the main tool connected to at least one secondary tool.

20 Claims, 2 Drawing Sheets

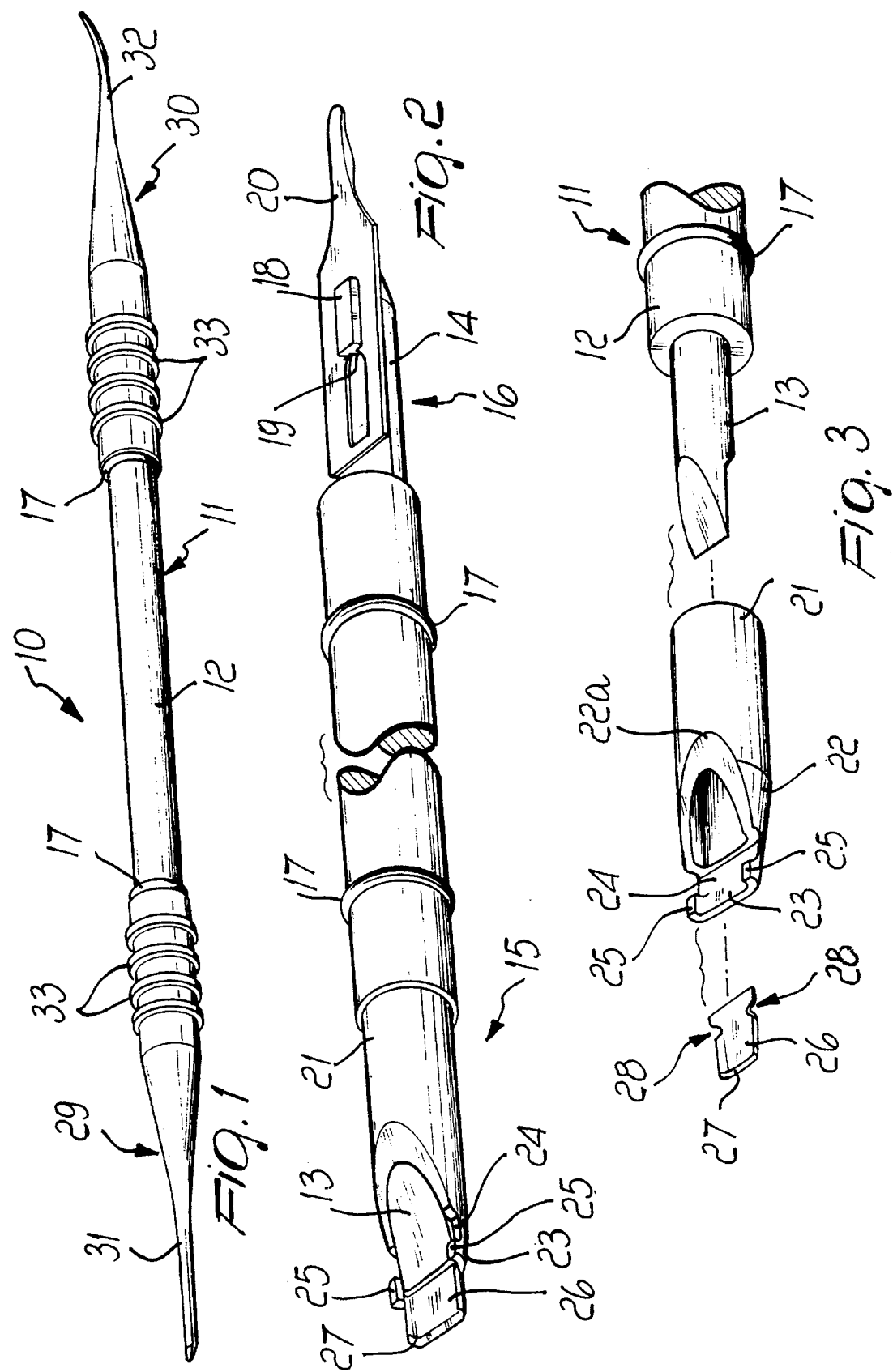

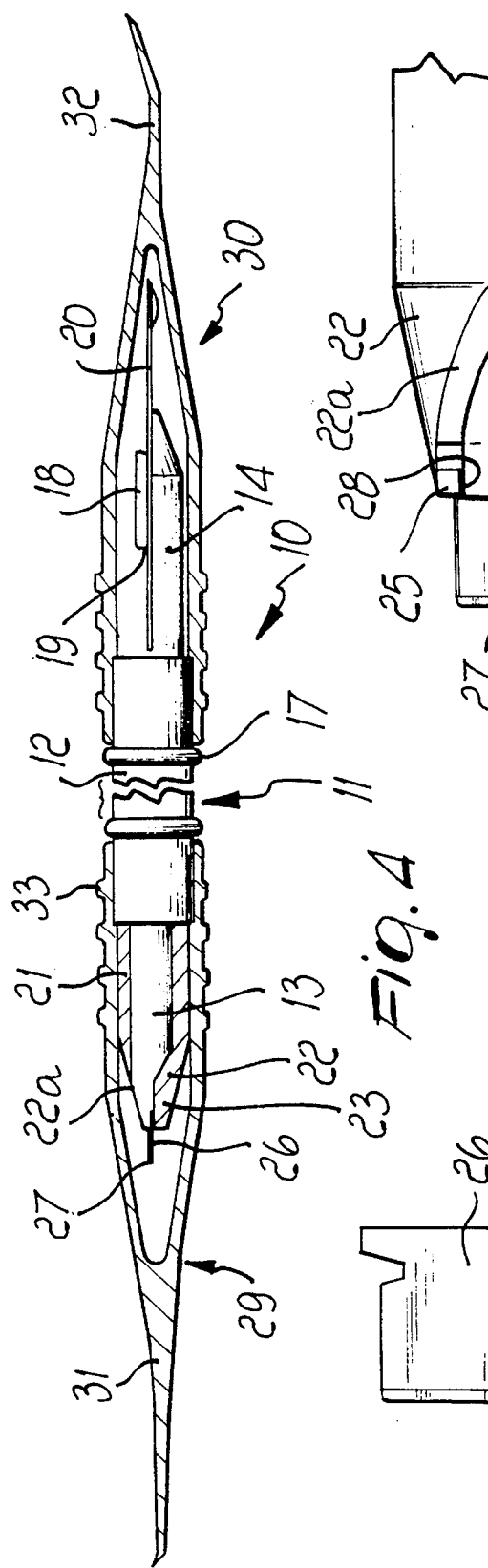

MULTI-FUNCTION INSTRUMENT FOR PEDICURE OPERATIONS OR THE LIKE

BACKGROUND OF THE INVENTION

The present invention relates to a multi-function instrument for pedicure operations or the like.

It is known that a wide range of substantially different operations is performed in the field of nonsurgical personal aesthetics, particularly for hands and feet, for example the removal of calluses and/or corny skin, nail cleaning and trimming, etcetera.

These operations require adequate tools having often very particular shapes.

Specifically in the field of pedicure, in addition to nail cleaning and trimming, operations such as for example the removal of plantar hyperkeratosis are also common.

It is therefore evident that pedicure, too, requires a wide range of instruments aimed at effectively performing various operations.

Several kinds of pedicure instruments are already commercially available.

However, all these known instruments have a single function.

More advanced types are also known, wherein the tool proper is interchangeable in order to perform different functions, which are all belonging, however, to the same category, such as for example cutting.

The above mentioned instruments, despite excellently performing their functions, have the substantial drawback that they achieve a low ratio between executable operations and number of instruments required to perform them.

Even in the most advanced types, although this ratio improves somewhat, instrument replacement is often difficult and slow.

SUMMARY OF THE INVENTION

The principal aim of the present invention is to provide a multi-function instrument which, without reducing its effectiveness in performing the intended functions, achieves a high ratio of operations executable with a single instrument.

Within the scope of this aim, an object of the present invention is to provide a multiple functionality that in no way penalizes the constructive simplicity of the instrument and its use.

Another object of the present invention is to provide a multi-function instrument that has a low cost and can be manufactured with known technologies.

Another object of the present invention is to provide a multi-function instrument that facilitates sterilization and is satisfactorily hygienic in use.

This aim, these objects, and others which will become apparent hereinafter are achieved by a multi-function instrument for pedicure operations or the like, according to the invention, which comprises a substantially rod-like body having at least one grip region and at least one region for coupling to at least one main blade-like tool, characterized in that it comprises at least one cap for said at least one main tool connected to at least one secondary tool.

BRIEF DESCRIPTION OF THE DRAWINGS

Further characteristics and advantages of the present invention will become apparent from the following detailed description of an embodiment thereof, illustrated only by way of non-limitative example in the accompanying drawings, wherein:

FIG. 1 is a perspective view of the multi-function instrument according to the invention;

FIG. 2 is a perspective view of the multi-function instrument according to the invention, without the protective caps;

FIG. 3 is an exploded view of a detail of the multi-function instrument according to the invention;

FIG. 4 is a sectional view, taken along a plane passing through a longitudinal axis of the multi-function instrument according to the invention;

FIG. 5 is a view of the detail of FIG. 3;

FIG. 6 is a view of two tools 26 after blanking from a razor blade;

FIG. 7 is a perspective view of a further embodiment of a multi-function instrument according to the invention.

DESCRIPTION OF THE PREFERRED EMBODIMENTS

With reference to the above figures, a multi-function instrument for pedicure operations or the like, according to the invention, is generally designated by the reference numeral 10.

The multi-function instrument 10 comprises a substantially cylindrical rod-like body 11, provided with a central grip region 12 and with ends 13 and 14 that constitute coupling regions for respective main tools 15 and 16.

An annular ridge 17 protrudes proximate to each end 13 and 14.

The end 14 is substantially bracket-shaped, and a raised portion 18, having a substantially mushroom-shaped transverse cross-section, protrudes from the surface of said bracket-shaped end.

The raised portion 18 is coupled to a slotted hole 19 shaped so as to taper in an end portion and provided in a lance-shaped interchangeable blade 20 having two opposite lateral cutting edges.

The blade 20 is fixed to the end 14 by forcing the raised portion 18 inside said tapering contoured portion of the slotted hole 19.

The end region 13, which has a smaller diameter than the central region 12, is substantially chisel-shaped and detachably couples without play to a substantially cylindrical sleeve 21 that abuts against the step formed by the difference in diameter between the region 12 and the end 13 and is therefore substantially coaxial to the body 11.

The sleeve 21 has an end 22 that is substantially frustum-shaped, with the exception of a portion 22a the shape wereof is obtained by cutting it along a plane inclined with respect to its longitudinal axis at an angle that is substantially equal to the angle of the chisel-like shape of the end 13.

A bracket 23 protrudes from the end 22, and two raised portions 25, arranged at the opposite sides of the bracket 23, are formed on the surface of said bracket that faces the longitudinal axis of the sleeve 21; a seat 24 arranged transversely with respect to the longitudinal axis of the sleeve 21 is also formed thereon.

A blade 26, which is fixed (but is optionally interchangeable in other embodiments) and obtained by blanking ordinary razor blades, is shaped complementarily with respect to the bracket 23 whereon it is mounted in an operating configuration.

Still in an operating configuration, the blade 26 is locked on the bracket 23 by means of the contrasting thrust applied thereto by the chisel-like shape of the end 13, which is inserted in the sleeve 21 in this configuration.

More particularly, the blade 26 comprises an active region, constituted by a cutting edge 27 that is substantially straight and lies transversely with respect to the longitudinal axis of the sleeve 21, and by an anchoring region, which lies substantially to the rear if the active region of the cutting edge 27 is considered as frontal; a substantially trapezoidal recess 28 is formed in said anchoring region at each lateral edge of the blade 26 and abuts against the raised portions 25 in the above mentioned operating configuration.

The multi-function instrument 10 also comprises two caps 29 and 30 which, when there is no need of using the main tools 15 and 16, cover the ends 13 and 14 to protect the operator from the risk of cuts and to protect the cutting edges from dents and contaminations not caused by their use.

More specifically, the caps 29 and 30 couple coaxially to the body 11 and abut against the corresponding raised portions 17.

The outside surfaces, in the end regions of said caps 29 and 30, are furthermore shaped so as to form a secondary tool.

In particular, the cap 29 has a tip 31 substantially straight and coaxial to the longitudinal axis of the body 11, whereas the cap 30 has a tip 32 slightly curved at its end.

Of course, the above described configurations of the caps 29 and 30 are mere examples and said caps may have the most disparate shapes.

Finally, both caps 29 and 30 have, on their outer surface, annular antislip grip ridges 33.

In the case described herein, the multi-function instrument 10 is disposable and is made of plastics and metals that can undergo gamma-ray sterilization.

With reference to FIG. 7, a further embodiment of a multi-function instrument, according to the invention, is generally designated by the reference numeral 100.

The multi-function instrument 100 comprises a rod-like body 101 having a central grip region 102 and ends 103 and 104; the end 103 constitutes a coupling region for an interchangeable tool (not shown in the figure) and a corresponding tool-shaped cap 105, whereas the end 104 is shaped so as to form a chisel-like instrument.

In practice it has been observed that the intended aim and objects of the present invention have been achieved.

It is in fact evident from the above description that a wide range of supports for an equally wide range of tools has been provided on a single body.

It should also be noted the extreme facility in changing the configuration of the multi-function instrument and therefore its functional capability.

The invention thus conceived is susceptible of numerous modifications and variations, all of which are within the scope of the inventive concept.

All the details may furthermore be replaced with other technically equivalent elements.

In practice, the materials employed, so long as they are compatible with the contingent use, as well as the dimensions, may be any according to the requirements.

What is claimed is:

1. Multi-function instrument for pedicure and manicure operations, comprising: a substantially rod-like body, said body having at least one grip region; at least one coupling region; at least one main tool for coupling to said coupling region; at least one cap for said at least one main tool; and at least one secondary tool, said at least one cap being connected to said at least one secondary tool;

wherein said at least one main tool comprises a blade fixed to said coupling region by means of an anchoring device, said anchoring device comprising a profiled sleeve that couples snugly and detachably to said coupling region and has a bracket-like protrusion, said coupling region being chisel-shaped, and said bracket-like protrusion including: a surface that faces a longitudinal axis of said sleeve; a seat arranged transversely with respect to the longitudinal axis of said sleeve; and two raised portions formed on said surface and arranged on opposite lateral edges of the bracket-like protrusion; said blade being shaped complementarily with respect to said bracket-like protrusion.

2. Multi-function instrument according to claim 1, wherein said body has a substantially cylindrical shape and comprises a central grip region and two end coupling regions.

3. Multi-function instrument according to claim 2, comprising two main tools, each tool being related to one of said two coupling regions.

4. Multi-function instrument according to claim 3, wherein one of said two main tools comprises a blade that is detachably fixed to one of said coupling regions through coupling means.

5. Multi-function instrument according to claim 3, comprising two secondary tools, each secondary tool being related to a said cap.

6. Multi-function instrument according to claim 5, wherein each one of said two secondary tools is monolithic with the corresponding one of said caps.

7. Multi-function instrument according to claim 5, wherein one of said two secondary tools is shaped so as to have a straight tip that is substantially coaxial to a longitudinal axis of said body.

8. Multi-function instrument according to claim 5, wherein a further one of said two secondary tools is shaped so as to have a tip that is curved with respect to the longitudinal axis of said body.

9. Multi-function instrument according to claim 1, wherein said blade is obtained by blanking ordinary razor blades.

10. Multi-function instrument according to claim 1, wherein said body has an end that is shaped so as to form a tool.

11. A multi-function instrument according to claim 1, which is made of metal and plastic materials that can undergo gamma-ray sterilization.

12. Multi-function instrument for pedicure and manicure operations, comprising: a substantially rod-like body, said body having at least one grip region; at least one coupling region; at least one main tool for coupling to said coupling region; at least one cap for said at least one main tool; and at least one secondary tool, said at least one cap being connected to said at least one secondary tool; wherein a first main tool comprises a blade that is detachably fixed to a first said coupling region through coupling means, and a second main tool comprises a blade fixed to a second said coupling region by means of an anchoring device, said blade being any one of the interchangeable and noninterchangeable type and obtainable by blanking ordinary razor blades.

13. Multi-function instrument according to claim 12, wherein said body has a substantially cylindrical shape and comprises a central grip region and two end coupling regions.

14. Multi-function instrument according to claims 12, comprising two secondary tools, each secondary tool being related to a said cap.

15. Multi-function instrument according to claim 14, wherein each one of said two secondary tools is monolithic with the corresponding one of said caps.

16. Multi-function instrument according to claim 14, wherein a first one of said two secondary tools is shaped so as to have a straight tip that is substantially coaxial to a longitudinal axis of said body, and a second one of said two secondary tools is shaped so as to have a tip that is curved with respect to the longitudinal axis of said body.

17. Multi-function instrument according to claim 12, wherein said anchoring device comprises a profiled sleeve that couples snugly and detachably to said coupling region and has a bracket-like protrusion, said coupling region being chisel-shaped.

18. Multi-function instrument according to claim 17, wherein said bracket-like protrusion has a surface that faces a longitudinal axis of said sleeve and whereon a seat, arranged transversely with respect to the longitudinal axis of said sleeve, and two raised portions, arranged on opposite lateral edges of said bracket-like protrusion, are formed, said interchangeable blade being shaped complementarily with respect to said bracket-like protrusion.

19. Multi-function instrument for pedicure and manicure operations, comprising: a substantially rod-like body extending along a longitudinal axis thereof, said body having at least one grip region; at least one end coupling region; at least one main tool for coupling to said end coupling region; at least one cap for said at least one main tool; and at least one secondary tool, said at least one cap being connected to said at least one secondary tool; wherein two main tools are provided, said main tools being each coverable by a respective said cap connected to a respective said secondary tool, with a first said secondary tool being shaped so as to have a straight tip that is substantially coaxial to said longitudinal axis of said body, and a second said secondary tool being shaped so as to have a tip that is curved with respect to said longitudinal axis of said body.

20. Multi-function instrument according to claim 19, wherein a first one of said two main tools comprises a blade that is detachably fixed to one of said coupling regions through coupling means, and a second one of said two main tools comprises a blade fixed to said coupling region by means of an anchoring device, said blade being any of an interchangeable and noninterchangeable type.

* * * * *